United States Patent [19]

Wreyford

[11] Patent Number: 5,152,963
[45] Date of Patent: Oct. 6, 1992

[54] TOTAL SULFUR ANALYZER SYSTEM OPERATIVE ON SULFUR/NITROGEN MIXTURES

[76] Inventor: Donald M. Wreyford, Antek Instruments, Inc., 6005 North Freeway, Houston, Tex. 77076

[21] Appl. No.: 86,262

[22] Filed: Aug. 17, 1987

Related U.S. Application Data

[62] Division of Ser. No. 893,089, Aug. 4, 1986, abandoned.

[51] Int. Cl.$^5$ .................... G01N 21/64; G01N 31/12
[52] U.S. Cl. ........................................ 422/80; 422/93; 436/123; 436/158; 436/122
[58] Field of Search ............... 436/122, 123, 158, 160, 436/172; 422/52, 78, 80, 93, 94

[56] References Cited

U.S. PATENT DOCUMENTS

| | | | |
|---|---|---|---|
| 3,795,812 | 3/1974 | Okabe | 250/373 |
| 3,838,969 | 10/1974 | Dugan | 422/78 X |
| 4,070,155 | 1/1978 | Fraim | 422/70 X |
| 4,077,774 | 3/1978 | Neti et al. | 436/172 X |
| 4,257,772 | 3/1981 | Bognin et al. | 422/80 X |
| 4,272,248 | 6/1981 | Neti | 436/172 X |
| 4,293,308 | 10/1981 | Sisti et al. | 422/80 K |
| 4,332,591 | 6/1982 | Oi et al. | 422/80 X |
| 4,401,763 | 8/1983 | Itoh | 422/80 X |
| 4,467,038 | 8/1984 | Scott | 422/80 X |

FOREIGN PATENT DOCUMENTS 1072772  3/1980  Canada.

Primary Examiner—Hill, Jr. Robert J.
Attorney, Agent, or Firm—Gunn, Lee & Miller

[57] ABSTRACT

A total sulfur analyzer system is set forth. The system operates with gas, liquid or solid samples including free sulfur, and sulfur and nitrogen compounds. The sample is first combusted to provide products of combustion including $SO_2$ and NO. The $SO_2$ quantity is measured by exposure to a particular frequency of ultraviolet light to obtain fluorescence, the fluorescent photons being measured by a photomultiplier tube (PMT). The system preferably includes suitable elecronics connected to the PMT for providing data of measurements of sulfur.

3 Claims, 1 Drawing Sheet

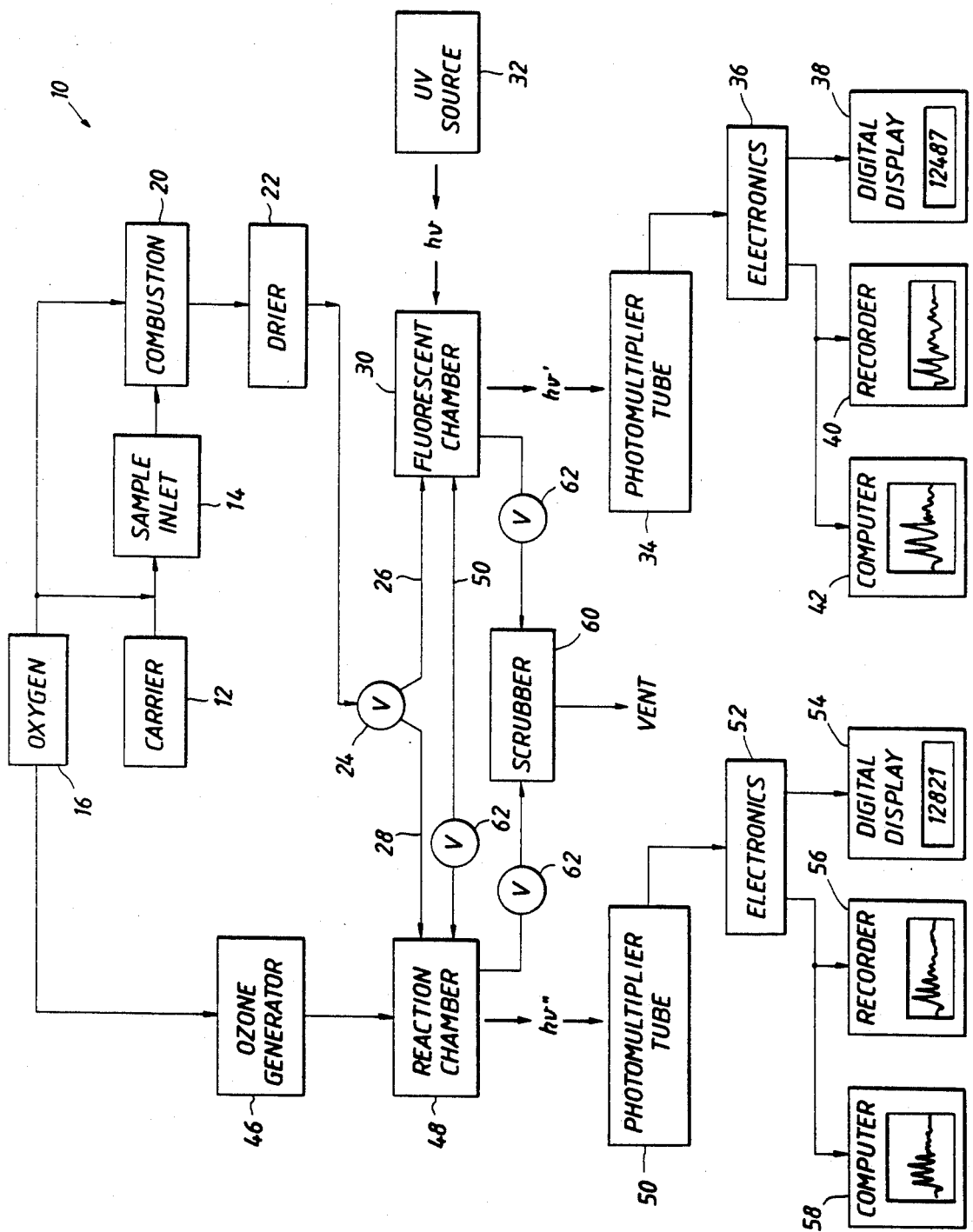

TOTAL SULFUR ANALYZER SYSTEM OPERATIVE ON SULFUR/NITROGEN MIXTURES

This is a divisional of application Ser. No. 893,089 filed Aug. 4, 1986 and now abandoned.

BACKGROUND OF THE DISCLOSURE

Sulfur and nitrogen compounds in organic and inorganic substances can often be pollutants. The risk and difficulties of such compounds requires analysis of a great variety of samples or specimens. There are various and sundry approaches to analysis of sulfur or nitrogen. They can range from the classical laboratory wet chemistry procedures to dedicated instrumentation. The type and approach selected in part depends on the expected range of concentration. It is unusual to find a system which can handle multiple element analysis over a wide dynamic range.

One device is a $SO_2$ pollution monitor for analysis of air, flue gas and the like. U.S. Pat. No. 3,795,812 is a device for inputting flue gas or the like. It detects only $SO_2$. It is not able to handle other sulfur compounds. Moreover, it is not able to handle sulfur in circumstances differing from flue gas or air monitoring. As an example, it cannot handle a liquid discharge which may or may not have $SO_x$ in it. Moreover, this is a limited device in the sense that it responds only to $SO_2$, not sulfur compounds of the general form of RS. Especially it is not able to handle RSN.

The present apparatus is additionally capable of handling a compound RSN, all of these being in various forms. In fact, the present apparatus is able to handle gases, liquids or solids which have sulfur or nitrogen or both therein either as a solid in mixture or as a compound. It applies to both organic and inorganic compounds, either alone or in mixture.

BRIEF SUMMARY OF THE DISCLOSURE

The disclosed system is a total sulfur analyzer capable of indication of sulfur, notwithstanding nitrogen in the sample. The system is useful for samples having the form of solid, liquid or gas. Moreover, it has a very wide dynamic range, for instance, the range is thought to extend as high as perhaps 20 to 25 percent sulfur and is believed reasonably accurate to less than about 0.5 ppm. Thus, this describes an analytical range of approximately $10^6$ for sulfur analysis. Separate nitrogen analysis range is perhaps $10^6$ or better.

The apparatus is summarized further as having a carrier gas source flowing past an inlet for the sample into a combustion chamber along with the flow of oxygen. The entire sample is combusted to provide combustion products. After they have been passed through a dryer, they are supplied to a valve and switched to first and second chambers. One chamber is a fluorescence chamber. The sample is irradiated with an ultraviolet source at a particular short wavelength. It absorbs the ultraviolet radiation and emits a longer wavelength which is observed by a photomultiplier tube to quantify the amount of sulfur present in the system. Another reaction chamber is included. It is supplied with a flow of ozone. The NO is converted to $NO_2^*$ in the presence of ozone and goes to ground state $NO_2$ accompanied by light emission by the chemiluminescent process. In that chamber, a separate photomultiplier tube observes the emitted photons and quantifies the nitrogen content. Interestingly, the combusted specimen can be provided to either chamber first and then the sample can be delivered to the other chamber for the second test. Performance of the first test does not interfere with performance of the second test.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawing.

It is to be noted, however, that the appended drawing illustrates only typical embodiments of this invention and are therefore not to be considered limiting of its scope, for the invention may admit to other equally effective embodiments.

The only drawing is a schematic block diagram of the total sulfur/nitrogen analyzer of the present disclosure.

DETAILED DESCRIPTION OF THE PREFERRED EMBODIMENT

Attention is first directed to the only view where the total analyzer for sulfur and nitrogen is identified by the numeral 10. The analyzer 10 incorporates several components which will be described in detail and some examples of its operation will then be given. A carrier gas source 12 provides an inert gas flow such as argon. It is delivered by a sample inlet means 14. This is supplied in conjunction with an optional flow of oxygen from an oxygen supply 16. The carrier gas conducts the flow of the sample and optional oxygen into a combustion means 20. Oxygen is provided to the means 20. Sample is combusted into various oxides.

The sample inlet means 14 may take different forms depending on the physical characteristics of the sample. A solid sample is best introduced by means of a quartz boat. Gases and liquids can be introduced through a sampling valve typically using a syringe to deliver the gas or liquid. A chromatographic separation can also be input for testing. A suitable combustion chamber is manufactured by Antek Instruments of Houston, Tex., and suitable models are 771C or 772C Pyro-Reactors. In the presence of oxygen, the sample is totally combusted. This process preferably takes place in the absence of a catalyst. In most circumstances a catalyst is deemed to be unnecessary and would ordinarily be an undue and unneeded complication. Moreover, the combustion preferably occurs at about 1,000° C. However, the range which is permitted can be as low as about 600° C. up to about 1500° C. Several things should be noted regarding this range. The upper end need not be precisely defined and can be varied even higher, for instance perhaps to 1600° C. It is sufficient to note that the temperature can be high enough that the various nitrogen and sulfur bonds in the compounds of the sample are broken and oxidation then converts into the various oxides as will be described. At the low end, approximately 600° C. is about the minimum at which conversion occurs. The volume of the sample is maintained relatively low in comparison with the carrier gas. Moreover, the amount of oxygen which is supplied is stoichiometric to assure complete conversion. If the chamber is well swept by the inflow of the sample along with the carrier gas, smooth ignition occurs and a relatively quick and uniform conversion of the sample is then obtained. Preferably, combustion occurs in a single step meaning that the sample which flows into the combustion means is converted in a continuous burning sequence. Retreatment thereafter is not needed.

In very general terms, the sample will be described as RSN to indicate that it is a compound, one or more. Free sulfur meaning sulfur in the free state can be tested. Free nitrogen typically is not included in the sample. That is, atmospheric nitrogen is so nearly inert that combination occurs at only extraordinarily high temperatures, those temperatures above the range mentioned above. It is therefore desirable to operate the combustion means at a temperature sufficiently high to combust all the sulfur, and all the nitrogen in compound form. The temperature is kept low enough that free nitrogen, typically atmospheric nitrogen, is not combusted. The compounds RSN, RN and also RS are combusted. It will form products of combustion including $CO_2$ and $H_2O$. These are meaningless to the subsequent analysis which occurs. Important products of combustion include $SO_2$ as well as NO. These will be discussed in detail hereinafter.

The combusted products flow from the combustion means 20 through a dryer 22. They are delivered to a switching valve 24. The switching valve directs the combusted sample including $SO_2$ and NO to either of two chambers. The sulfur analysis chamber will be described first. Moreover, the sequence of testing for sulfur and nitrogen will be discussed in detail.

The valve 24 can be switched to supply the combustion products through a sample line 26. Following the sample line 26, it connects with a fluorescence chamber 30. In the fluorescence chamber, $SO_2$ is exposed to an ultraviolet light source 32 which is coupled into the chamber from a suitable light source. This dry sample may include $SO_2$. Under the assumption that it is present, ultraviolet radiation of a particular wavelength is absorbed by the $SO_2$ molecule and is subsequently reemitted at a longer wavelength. This interchange is known as fluorescence and is specific for $SO_2$. The preferred wavelength for the ultraviolet radiation from the source 32 is 213.8 nanometers. This radiation wavelength serves to excite tho $SO_2$ molecule. It causes subsequent radiation but at a longer wavelength. This fluorescence phenomena has a spectrum which spans approximately 214 nanometers to up to about 440 nanometers. The peak fluorescent wavelength is about 320 nanometers for $SO_2$. The ultraviolet source 32 is preferably a zinc discharge lamp maintained on a highly stabilized power supply to assure emission of the proper light spectrum. A 214 nanometer interference filter is used to narrow the frequency content of the ultraviolet radiation from the source.

The fluorescence chamber introduces the flowing gas sample into an exposed area where a suitable window into the chamber enables the irradiating light to fall on the flowing sample. The chamber 30 is typically provided with two windows. The first window just described permits the selected wavelength of ultraviolet irradiation to enter the chamber from the source 32. The second window is used to provide a field of vision or view for a photomultiplier tube (PMT) 34. The PMT 34 observes the spectrum of the fluorescence radiation and provides an output or quanta indicative of the fluorescence phenomenon. As desired, the PMT can be behind a selective filter. It is convenient to try to isolate the peak in the fluorescent emission band and thus the filter can have a peak sensitivity of about 320 nanometers. This enables the PMT to pick up the greater quanta of photons emitted from the irradiated sample and provide an output that is indicative of $SO_2$ content. The PMT 34 is provided with a suitable amplifier circuit 36. The data is converted into amplified peak pulses which are supplied to a digital display 38. It is also supplied to a recorder 40, and can be conveniently input to a computer 42 for additional storage or formatting and presentation.

Continuing now with an additional description of the apparatus, the numeral 46 identifies an ozone generator. It supplies ozone to a reaction chamber 48. The sample line 26 provides the sample to the reaction chamber 30. The reaction chamber 30 is connected with the reaction chamber 48 by means of a line 50. Alternate flow paths involving the valve 24 and the line 50 will be described hereinafter. The chamber 48 has a window in it with a PMT 50 located to observe chemiluminescent flashes from the chamber 48. The PMT 50 is connected with suitable amplifier circuitry 52. That circuit in turn is connected with a suitable digital display 54. The data is also provided to a recorder 56 and to a suitable computer 58 to be formatted and stored. The reaction occurring in the chamber 48 involves the emission of chemiluminescent light photons as will be described. The apparatus additionally includes a scrubber 60 which has a vent for discharge of the spent sample gases. There are three plug valves 62 which are switched to control flow.

There are two flow routes through the apparatus. The flow routes connect the chambers 30 and 48 in one sequence or the reverse. The flow routes thus enable testing for sulfur first in the chamber 30 or nitrogen first in the chamber 48. The flow routes include the valve 24 which is switched to deliver the sample either through the sample line 26 or the similar sample line 28. The first route uses the sample line 26 which delivers the sample to the chamber 30. After the sulfur content has been measured, the sample is then delivered by the line 50 to the chamber 48 for testing of nitrogen content. It then flows to the scrubber and is discharged. A second flow route extends from the valve 24 through the sample line 28 and into the chamber 48. It then can flow through the line 50 to the chamber 30 so that the testing sequence provides first a measure of nitrogen content and secondly a measure of sulfur content. Then, the discharged gases can flow to the scrubber 60. The two flow routes are included subject to control of the valve 24 and the plug valves 62. No bias or prejudice attaches to the conduct of one test in advance of the other. The reason for this is described in detail regarding the independence of the two analytical tests and the fact that they are unique to the particular compounds in question.

The apparatus can be used to conduct only a single test. If that is the fact, it is not necessary to operate the test apparatus for the particular element where no test data is required. To this end, the route can be through the valve 24 and then into either of the sample lines 26 or 28 to respective chambers connected thereto and to the scrubber 60. In that instance, transfer from chamber to chamber is not required. The line 50 can be used for bidirectional flow. It connects the two chambers together so that the sample flows through the first chamber and then through the second. It is a matter of indifference in the operation of the line 50 which chamber is provided with the sample first. Through illustrated valving, the spent sample can then be delivered at the end of testing through the scrubber 60 and then vented.

Assume that the material being tested is represented by the general representation of RSN. RSN is combusted in the presence of oxygen at an elevated temperature to yield various combustion products, and those of particular importance to this disclosure include $SO_2$ and NO. Water is removed by the dryer and $CO_2$ is meaningless to the subsequent events. Assume that the sample also may or may not have elemental sulfur with it. That also is converted to $SO_2$. The sulfur and nitrogen compounds are then tested and quantified by the following two relationships:

  (1)

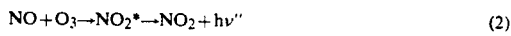  (2)

In Equation (1) above, it will be observed that sulfur is irradiated by the ultraviolet light at the frequency above described. This preferred frequency initiates fluorescence, and the emitted light is then observed by the PMT 34. This is represented symbolically in the drawing with respect to the chamber 30. Thus, if there is no $SO_2$ present, the PMT 34 will not have a measured output. It will not observe anything. $SO_2$ present in the chamber 30 is quantified by the photons emitted by the $SO_2$ and observed by the PMT 34. This data is amplified by the electronics 36 and then is handled in any suitable fashion desired including display of peaks by the display 38. The data can be recorded as a function of time by the recorder 40. It is typically stored and presented in a suitable format by a computer 42.

In the chamber 48, Equation (2) describes the conversion which occurs there. Briefly, the $O_3$ introduced from the generator 46 reacts with NO to provide $NO_2^*$. The $NO_2^*$ goes to ground state $NO_2$. Light is emitted in a known spectrum. The PMT 50 (typically with a suitable selective filter) counts the pulses provided from the chamber 48. These pulses are emitted as a result of the chemiluminescent transaction occurring in the chamber 48. The pulses are counted as a function of time and provide a measure of bound nitrogen content in the sample. As before, the peak value can be displayed at 54. The data is recorded as a function of time by the recorder 56 and can be stored and presented in any suitable format by the computer 58.

Modes of operation primarily remain the same other than switching of the valve 24. It is a matter of indifference on observing Equations (1) and (2) as to which is implemented first. Assume that there are both $SO_2$ and NO in the sample from the combustion means 20. Assume that the valve 24 is operated to deliver the sample to the chamber 30 first. Irradiation from the light source 32 has no impact on the NO in the sample. It is unaltered by this. Thus, the data measuring the presence of sulfur is obtained but the NO content is not changed or modified. This permits the sulfur test to occur first. It does not bias the data in measurement of nitrogen content.

If the valve 24 is operated so that the nitrogen test is performed first, Equation (2) shows the conversion which occurs there. There is a preference for the $O_3$ to combine the NO. Thus, Equation (2) above occurs and the nitrogen data is obtained. Even though the $O_3$ conversion in the chamber 48 is exothermic and even though the chamber 48 may be maintained of an elevated temperature, the $SO_2$ present in the sample is not impacted by the chemiluminescent emission described in Equation (2). Thus, the nitrogen test can be performed first, and the $SO_2$ in the sample is unaltered so that the sulfur data remains true and accurate. This thereby permits either test to be conducted first and the second test is not biased by the performance of the first test.

If one is certain that the sample includes only nitrogen or sulfur but not both, then the equipment not needed can simply be turned off. In that instance, the valve 24 can be conveniently switched to deliver the sample to the first of interest for performing only that test.

The total sulfur/nitrogen analyzer 10 of this disclosure can be conveniently mounted in a single housing. Conveniently, the components connected from the PMTs 34 and 50 are substantially identical and can be made in duplicate fashion.

| TABLE SULFUR/NITROGEN DATA |||
| Sample | ppm Sulfur | ppm Nitrogen |
| --- | --- | --- |
| A | 4486 +/− 34 | 492 +/− 4 |
| B | 593 +/− 4 | 1029 +/− 11 |
| C | 20375 +/− 131 | 27 +/− 0.5 |
| D | 11623 +/− 81 | 184 +/− 2 |

A & B are gas oil samples.
C & D are synthetic samples.

Typical performance is described. The table shows four typical samples. In the four samples, it will be noted that the relative relationship between sulfur and nitrogen varies significantly. The samples do not begin to exercise the full dynamic range of the apparatus. As mentioned earlier, sulfur measurements down into the range of less than 1 ppm are believed to be available with a high measure of accuracy. Sulfur measurements can range as high as perhaps 25 percent of the sample. In testing for accuracy, sulfur samples tested through the means 10 and then compared with data from x-ray fluorescence, utilizing multiple repetitive testing and identical samples show a correlation accuracy with an error of less than about +/− one percent. Cautiously, it is reasoned that this system provides an accuracy of +/− two percent in contrast with other sulfur measuring techniques. It has an advantage, however, over x-ray fluorescence, namely that the dynamic range appears to be $10^6$ or greater. X-ray fluorescence does not have that wide a dynamic range. Indeed, the present approach seems to show a dynamic range which is wider than any other sulfur analytical approach available.

While the fore going is directed to the preferred embodiment, the scope is determined by the claims which follow.

What is claimed is:

1. A total sulfur testing analyzer for testing for total sulfur content of a sample containing elemental or chemically bound sulfur therein, the analyzer comprising:
   (a) sample inlet line means for receiving a sulfur containing sample;
   (b) combustion means connected to said sample inlet line means for burning the sample to form combustion products including $SO_2$;
   (c) a combustion product flow line connected to remove all combustion products from said combustion means;
   (d) chamber means connected to said flow line for receiving combustion products therethrough;
   (e) light source means for forming light having a wavelength to irradiate $SO_2$, said light means positioned to light said chamber means for SO$_2$ irradiation therein;

(f) light detector means observing SO$_2$ after irradiation by said light source means for observing any fluorescence emitted by irradiated SO$_2$;

(g) circuit means connected to said light detector means for forming a signal quantifying any irradiated SO$_2$ fluorescence emitted thereby;

(h) a dryer connected to said combustion means to receive the combustion products therefrom to remove water from the combustion products;

(i) valve means connected to said dryer and having two outlet ports, one of said ports being connected with said chamber means for delivery of the combustion products to said chamber means;

(j) a separate reaction chamber connected to the second of said output ports for delivery of the combustion products to the reaction chamber for separate testing for constituents other than sulfur; and (k) flow line means connected from said reaction chamber and connected to said chamber means for delivery of the combustion products to said chamber means after passing through said reaction chamber.

2. The apparatus of claim 1 including a vented scrubber connected to said chamber means and said reaction chamber for discharging combustion products therefrom after scrubbing.

3. The apparatus of claim 2 further including valve means in said flow line means.

* * * * *